(12) United States Patent
Blass

(10) Patent No.: US 6,537,969 B1
(45) Date of Patent: Mar. 25, 2003

(54) NUTRITIONAL SUPPLEMENT FOR CEREBRAL METABOLIC INSUFFICIENCIES

(75) Inventor: John P. Blass, One Orchard Pl., Bronxville, NY (US) 14850

(73) Assignee: John P. Blass, Bronxville, NY (US)

( * ) Notice: Subject to any disclaimer, the term of this patent is extended or adjusted under 35 U.S.C. 154(b) by 0 days.

(21) Appl. No.: 09/529,091

(22) PCT Filed: Sep. 1, 1998

(86) PCT No.: PCT/US98/18120

§ 371 (c)(1),
(2), (4) Date: Oct. 20, 2000

(87) PCT Pub. No.: WO99/21565

PCT Pub. Date: May 6, 1999

Related U.S. Application Data

(60) Provisional application No. 60/063,165, filed on Oct. 24, 1997.

(51) Int. Cl.[7] .................... A61K 31/05; A61K 31/194; A61K 31/01
(52) U.S. Cl. .................... 514/23; 514/574; 514/733
(58) Field of Search .................... 514/574, 23, 733

(56) References Cited

U.S. PATENT DOCUMENTS 3,963,579 A  6/1976  Umezawa et al. ........ 195/80 R
5,589,182 A  * 12/1996  Tashiro et al. .............. 424/423

OTHER PUBLICATIONS

Thurston et al., J. Cereb. Blood Flow Metab., 3(4), 498–506 (1983) (abstract).*

Yokota et al., *Chemical Abstracts*, 119:25945, "Abnormal Metabolism of Carbohydrate and Fatty Acid in Mitochondrial Disorders," *Nippon Iyo Masu Supekutoru Gakkai Koenshu*, 17:55–61 (1992).

R. Luft, "The Development of Mitochondrial Medicine," *Proc. Natl. Acad. Sci. USA* 91:8731–8738 (1994).

A. Nordberg, "Pharmacological Treatment of Cognitive Dysfunction in Dementia Disorders," *Acta Neurol. Scand.* Suppl 168:87–92 (1996).

* cited by examiner

*Primary Examiner*—Phyllis G. Spivack
(74) *Attorney, Agent, or Firm*—Nixon Peabody LLP

(57) ABSTRACT

The present invention relates to a pharmaceutical composition which consists essentially of glucose and malic acid. The present invention also relates to administration of the pharmaceutical composition to treat an individual for a disorder involving impaired mitochondrial function and to improve cerebral function in an individual having impaired cerebral metabolism.

45 Claims, 1 Drawing Sheet

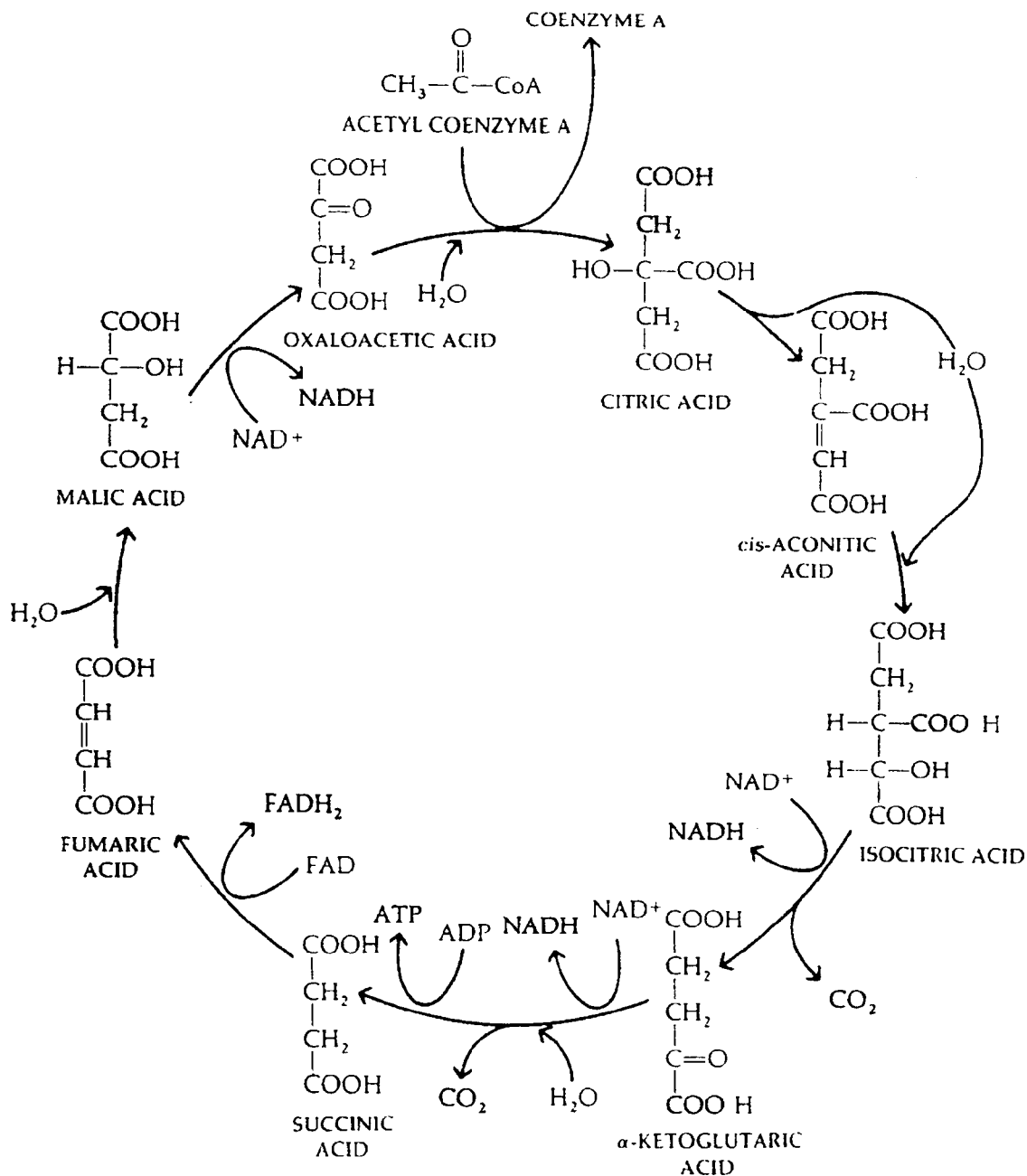

NUTRITIONAL SUPPLEMENT FOR CEREBRAL METABOLIC INSUFFICIENCIES

This application claims the benefit of U.S. Provisional Patent Application No. 60/063,165, filed Oct. 24, 1997.

FIELD OF THE INVENTION

The present invention relates to nutritional supplements for individuals suffering from cerebral metabolic insufficiencies and methods of treating disorders indicated by cerebral metabolic insufficiencies.

BACKGROUND OF THE INVENTION

During normal operation of the catabolic process, energy is harvested and subsequently stored in a readily available form, namely, the phosphate bonds of adenosine triphosphate ("ATP"). When energy is required for anabolic processes, a phosphate bond of ATP is broken to yield energy for driving anabolic reactions and adenosine diphosphate ("ADP") is regenerated. The process of catabolism involves the breakdown of proteins, polysaccharides, and lipids. Proteins are broken into smaller peptides and constituent amino acids, polysaccharides and disaccharides are broken down into their monosaccharide constituents, and lipids are broken down into glycerol and the fatty acid constituents. These compounds are further broken down into even smaller compounds, principally, two-carbon acetyl groups.

The two-carbon acetyl group, an essential component in the catabolic process, is introduced into the Krebs tricarboxylic acid cycle ("Krebs cycle") via acetyl coenzyme A. The acetyl group serves as a carbon source for the final stages of catabolism. The Krebs cycle and an accompanying electron transport system involve a series of enzymatically controlled reactions which enable complete oxidation of the two-carbon acetyl group to form carbon dioxide and water. As shown in FIG. 1, acetyl groups are introduced into the Krebs cycle by bonding to oxaloacetic acid to form citric acid. During subsequent steps of the Krebs cycle, citric acid is converted into aconitic acid and then isocitric acid or, alternatively, it is converted directly into isocitric acid. As isocitric acid is converted into ketoglutaric acid, one carbon atom is completely oxidized to carbon dioxide. As ketoglutaric acid is converted into succinic acid, a second carbon atom is completely oxidized to carbon dioxide. During the remaining steps, succinic acid is converted into fumaric acid, fumaric acid is converted into malic acid, and malic acid is converted into oxaloacetic acid. Each complete turn of the Krebs cycle harvests the energy of the acetyl group to yield one molecule of ATP, three molecules of nicotinamide adenine dinucleotide ("NADH"), and one molecule of flavin adenine dinucleotide $FADH_2$. The NADH and $FADH_2$ are subsequently used as electron donors in the electron transport system to yield additional molecules of ATP.

The Krebs cycle and the accompanying electron transport system occur in the mitochondria, which are present in different types of cells in varying numbers depending upon the cellular energy requirements. For example, neuronal and muscle cells have high numbers of mitochondria because they have extremely high energy requirements. Because of their high energy requirements, these types of cells are particularly vulnerable to disorders or conditions associated with a breakdown of the catabolic pathways or otherwise defective intracellular energy metabolism. Exemplary disorders or conditions include Alzheimer's Disease ("AD"), Parkinson's Disease ("PD"), Huntington's Disease ("HD"), and other neurodegenerative disorders (Beal et al., "Do Defects in Mitochondrial Energy Metabolism Underlie the Pathology of Neurodegenerative Diseases?," *Trends Neurosci.* 16(4):125–131 (1993); Jenkins et al., "Evidence for Impairment of Energy Metabolism in vivo in Huntington's Disease Using Localized $^1$H NMR Spectroscopy," *Neurol.* 43:2689–2695 (1993)).

AD is one of the most commnon causes of disabling dementia in humans. Because AD is a progressive, degenerative illness, it affects not only the patient, but also their families and caregivers. In early stages of AD, activities of daily living ("ADLs") are only minimally affected by cognitive or functional impairment, which may often be a first clinical sign of the disease (Small et al., "Diagnosis and Treatment of Alzheimer Disease and Related Disorders," Consensus Statement of the American Association for Geriatric Psychiatry, the Alzheimer's Association, and the American Geriatrics Society, *JAMA* 278:1363–1371 (1997)). As AD progresses, the patients' ability to perform ADLs diminishes and they become increasingly more dependent upon caregivers and other family members (see Galasko et al., "An Inventory to Assess Activities of Daily Living for Clinical Trials in Alzheimer's Disease," *Alzheimer Dis. Assoc. Disord.* 11 (Suppl. 2):S33–S39 (1997)).

PD is widely considered to be the result of degradation of the pre-synaptic dopaminergic neurons in the brain, with a subsequent decrease in the amount of the neurotransmitter dopamine that is being released. Inadequate dopamine release, therefore, leads to the onset of voluntary muscle control disturbances symptomatic of PD. The motor dysfunction symptoms of PD have been treated in the past using dopamine receptor agonists, monoamine oxidase binding inhibitors, tricyclic antidepressants, anticholinergics, and histamine H1-antagonists. Unfortunately, the main pathologic event, degeneration of the cells in substantia nigra, is not helped by such treatments. The disease continues to progress and, frequently after a certain length of time, dopamine replacement treatment will lose its effectiveness. In addition to motor dysfunction, however, PD is also characterized by neuropsychiatric disorders or symptoms. These include apathy-amotivation, depression, and dementia. PD patients with dementia have been reported to respond less well to standard L-dopa therapy. Moreover, these treatments have little or no benefit with respect to the neuropsychiatric symptoms.

HD is a familial neurodegenerative disorder that afflicts about 1/10,000 individuals (Martin et al., "Huntington's Disease: Pathogenesis and Management," *N. Engl. J. Med.* 315:1267–1276 (1986); Gusella, "Huntington's Disease," *Adv. Hum. Genet.* 20:125–151 (1991)). It is inherited in an autosomal dominant manner and is characterized by choreiform movements, dementia, and cognitive decline. The disorder usually has a mid-life onset, between the ages of 30 to 50 years, but may in some cases begin very early or much later in life. The symptoms are progressive and death typically ensues 10 to 20 years after onset, most often as the result of secondary complications of the movement disorder. The major site of pathology in HD is the striatum, where up to 90% of the neurons may be depleted. The impaired cognitive functions and eventual dementia may be due either to the loss of cortical neurons or to the disruption of normal activity in the cognitive portions of the basal ganglia. The characteristic chorea is believed to be caused by the neuronal loss in the striatum, although a reduction in subthalamic nucleus activity may also contribute.

Glutamate-induced neuronal cell death is believed to contribute to HD. Glutamate is the principal excitatory transmitter in the brain. It excites virtually all central neurons and is present in the nerve terminals in extremely high concentrations ($10^{-3}$M). Glutamate receptors are divided into four types (named after their model agonists): kainate receptors, N-methyl-D-aspartate ("NMDA") receptors, α-amino-3-hydroxy-5-methyl-4-isoxazolepropionate ("AMPA") receptors, and metabolotrophic receptors. Many normal synaptic transmission events involve glutamate release. However, glutamate can also induce neurotoxicity and neuronal death at high levels (Choi, "Glutamate Neurotoxicity and Diseases of the Nervous System," Neuron, 1:623–634 (1988)). The mechanism of cell death occurs primarily by the persistent action of glutamate on the NMDA receptors. These toxic changes produced by glutamate, called glutamate excitotoxicity, are believed to be the cause of cell damage and death after acute brain injury such as stroke or excessive convulsions. It has been suggested that excitotoxicity may be involved in brain ischemia, AD, and HD (Greenamyre et al., "Alterations in L-glutamate Binding in Alzheimer's and Huntington's Diseases," Science, 227:1496–1499 (1985); Choi, "Glutamate Neurotoxicity and Diseases of the Nervous System," Neuron, 1:623–634 (1988)).

The administration of agents that improve energy metabolism, and possibly prevent cell death, has been suggested for the treatment of disorders characterized by energy-deficient cells (Beal et al., "Do Defects in Mitochondrial Energy Metabolism Underlie the Pathology of Neurodegenerative Diseases?," Trends Neurosci. 16(4):125–131 (1993)). One approach to augmenting the energy level of energy-deficient cells (i.e., as a result of hypoxia or hypoglycemia) involves the administration of pyruvate, which is later converted to acetate during normal metabolism. According to U.S. Pat. No. 5,395,822 to Izumi et al. ("Izumi"), the administration of pyruvate to a patient before or after an ischemic event (i.e., which produces a state of hypoxia or hypoglycemia) is sufficient to prevent neuronal degradation that normally is associated with the ischemic event. Izumi also identified the administration of glucose prior to an ischemic event as undesirable, because its administration resulted in lactic acidosis, which is a factor contributing to brain damage.

An approach for the treatment of AD includes the administration of NADH or nicotinamide adenine dinucleotide phosphate ("NADPH"), or the salts thereof. The administration of NADH or NADPH is described in U.S. Pat. No. 5,444,053 to Birkmayer, which discloses the use of salts formed with various acids including, among others, malic acid, succinic acid, and acetic acid. Similar approaches to treating PD using NADH and NADPH are described in U.S. Pat. Nos. 5,019,561 and 4,970,200, both to Birkmayer.

The present invention is directed toward overcoming these above-noted deficiencies in treating conditions associated with a breakdown of the catabolic pathways or otherwise defective intracellular energy metabolism.

SUMMARY OF THE INVENTION

The present invention relates to a pharmaceutical composition which includes a sugar and a Krebs cycle intermediate or salt thereof, or a precursor of a Krebs cycle intermediate. Krebs cycle intermediates include citric acid, aconitic acid, isocitric acid, α-ketoglutaric, succinic acid, fumaric acid, malic acid, oxaloacetic acid, and mixtures thereof. Precursors of Krebs cycle intermediates are compounds which, upon administration to a subject, are converted by the body to form a Krebs cycle intermediate.

The present invention also relates to a method of treating impaired mitochondrial function. The method includes administering a pharmaceutical composition of the present invention to a subject having a disorder involving impaired mitochondrial function under conditions effective to improve mitochondrial function.

The present invention further relates to a method of improving cerebral function in an individual having impaired cerebral metabolism. This method includes administering a pharmaceutical composition of the present invention to a subject having impaired cerebral metabolism under conditions effective to improve cerebral function.

The pharmaceutical compositions of the present invention are particularly desirable for the prophylaxis or treatment of disorders associated with impaired mitochondrial function. Disorders that can be treated include conditions or diseases characterized by a decreased level of oxidative metabolism, such as conditions or diseases of the nervous system, conditions or diseases of other parts of the body (e.g., cardiovascular disorders, musculoskeletal disorders, etc.), and conditions or diseases of the body as a whole. The pharmaceutical composition is particularly desirable for use in treating nervous system disorders that are indicated by symptoms of dementia. Upon administration of the pharmaceutical compositions of the present invention, it is possible to reduce the severity of dementia through enhancing cerebral cellular metabolism (i.e., improving mitochondrial function in cerebellar tissues). Thus, the pharmaceutical compositions are particularly useful as a prophylactic for delaying the onset of dementia or as a treatment for delaying the progression of dementia associated with various nervous system disorders. The pharmaceutical compositions are also useful for ameliorating the clinical manifestations of dementing illnesses by improving the function of the remaining, but often metabolically compromised, cells.

BRIEF DESCRIPTION OF THE DRAWINGS

FIG. 1 illustrates the Krebs cycle and the relationship between each of its intermediates. Oxaloacetic acid and an acetyl group (from acetyl-CoA) combine to form citric acid. In the course of the cycle, two of the carbon atoms of citric acid are oxidized completely to carbon dioxide, and oxaloacetic acid is regenerated. This process generates one molecule of ATP, three molecules of NADH, and one molecule of $FADH_2$. Ultimately, the reduced cofactors NADH and $FADH_2$ are introduced into an electron transport mechanism that results in their oxidation, which yields additional molecules of ATP.

DETAILED DESCRIPTION OF THE INVENTION

The present invention relates to a pharmaceutical composition which includes a sugar in combination with a Krebs cycle intermediate or a precursor of a Krebs cycle intermediate.

Krebs cycle intermediates are the acids or salts of compounds which are utilized during the Krebs cycle. Thus, Krebs cycle intermediates include citric acid, aconitic acid, isocitric acid, α-ketoglutaric acid, succinic acid, fumaric acid, malic acid, oxaloacetic acid, or mixtures thereof. Referring again to FIG. 1, depending upon which Krebs cycle intermediate the pharmaceutical composition of the present invention contains, the pharmaceutical composition will be predicted ultimately to yield differing amounts of ATP. It is believed that a number of disorders involving altered oxidative metabolism include a disruption of the Krebs cycle at or prior to conversion of α-ketoglutaric acid to succinic acid. For such disorders, the pharmaceutic compositions of the present invention preferably contain a Krebs cycle intermediate such as succinic acid, fumaric acid, malic acid, oxaloacetic acid, or mixtures thereof.

Precursors of Krebs cycle intermediates are compounds which upon administration to a subject are converted by the body (i.e., in vivo) into a Krebs cycle intermediate. Generally, mono- and di-alkyl citrates, aconitates, isocitrates, α-ketoglutarates, succinates, fumarates, malates, and oxaloacetates are desirable precursors because the ester-bonds are readily broken by the body to yield the Krebs cycle intermediate. Other ester precursors may be developed using known technology for enhancing entry of the precursor molecule into affected cells. For example, U.S. Pat. No. 5,739,117 to Yokoyama, which is hereby incorporated by reference, discloses a variety of glucose ester derivatives which more effectively enter brain cells. One preferred class of precursors of Krebs cycle intermediates are compounds which are converted by the body into oxaloacetic acid or oxaloacetate. Exemplary precursors in this class include 2-keto-4-hydroxypropanol, 2,4-dihydroxybutanol, 2-keto-4-hydroxybutanol, 2,4-dihydroxybutyric acid, 2-keto-4-hydroxybutyric acid, aspartates, as well as the previously identified mono- and di-alkyl oxaloacetates. The amino acid aspartate is converted into oxaloacetic acid by the transamination reaction.

Sugars which are suitable for use with the present invention include monosaccharides, such as glucose, fructose, mannose, and galactose; disaccharides such as sucrose, maltose, and lactose; and polysaccharides (i.e., starches such as amylose) that are digested by the body to form monosaccharides.

The pharmaceutical composition of the present invention can also include an adjuvant for enhancing mitochondrial function (i.e., oxidative metabolism). Suitable adjuvants include vitamins, minerals, antioxidants, and other metabolism-enhancing compounds. B-complex vitamins are preferred for administration as adjuvants because of their involvement with metabolism. Exemplary vitamins which are useful as an adjuvant include thiamin (vitamin $B_1$), riboflavin (vitamin $B_2$), niacin (Vitamin $B_3$), pyridoxine derivatives (vitamin $B_6$), and pantothenic acid. Exemplary minerals which are useful as an adjuvant include calcium, magnesium, sodium, potassium, and zinc. Exemplary antioxidants include ascorbic acid, alpha-tocopherol, resveratrol, quercetin, and other flavonoids. Exemplary metabolism-enhancing compounds include L-carnitine and its derivatives, and creatine. Creatine supplementation is described in U.S. Pat. No. 5,767,159 to Hultman, which is hereby incorporated by reference. L-carnitine has been found to ameliorate abnormalities associated with AD in a model system (Malow et al., "Cultured Cells as a Screen for Novel Treatments of Alzheimer's Disease," *Arch. Neurol.* 46:1201–1203 (1989), which is hereby incorporated by reference).

The pharmaceutical composition of the present invention can be administered orally, by anal suppository, parenterally, for example, subcutaneously, intravenously, intramuscularly, intraperitoneally, intrathecally, by interstitial infusion, by intranasal instillation, or by application to mucous membranes, such as that of the nose, throat, and bronchial tubes. They may be administered alone or with suitable pharmaceutically-acceptable vehicles, and can be in solid or liquid form such as tablets, capsules, powders, solutions, suspensions, or emulsions.

The solid unit dosage forms can be of the conventional type, such as an ordinary gelatin type containing the Krebs cycle intermediate or the precursor of a Krebs cycle intermediate and a pharmaceutically acceptable vehicle. Suitable vehicles include lubricants and inert fillers. The above described sugars can also serve as fillers. In another embodiment, these compounds are tableted with conventional tablet bases (i.e., sugars as described above) in combination with binders like acacia, gum tragacanth, cornstarch, or gelatin; disintegrating agents such as cornstarch, potato starch, or alginic acid; a lubricant like stearic acid or magnesium stearate; and sweetening agents such as the above described sugars, saccharine, or aspartame; and flavoring agents such as peppermint oil, oil of wintergreen, or artificial flavorings.

The pharmaceutical compositions of the present invention may also be administered in injectable dosages by solution or suspension of these materials in a physiologically acceptable diluent with a pharmaceutical vehicle. Such vehicles include sterile liquids such as water and oils, with or without the addition of a surfactant and other pharmaceutically acceptable adjuvants such as those described above. Illustrative oils are those of petroleum, animal, vegetable, or synthetic origin, for example, peanut oil, soybean oil, or mineral oil. In general, water, saline, aqueous sugar solutions formed with the above-described sugars, and glycols such as polypropylene glycol or polyethylene glycol, are preferred liquid vehicles, particularly for injectable solutions. To maintain sterility and prevent action of microorganisms, antibacterial and antifungal agents, such as parabens, chlorobutanol, phenol, ascorbic acid, thimerosal, and the like may be added to the vehicle.

The pharmaceutical composition of the present invention is useful for augmenting cellular metabolism in subjects (e.g., patients) who suffer from a disorder characterized by abnormally decreased levels of oxidative metabolism. It is believed that administration of the pharmaceutical composition of the present invention enhances mitochondrial function by augmenting operation of the Krebs cycle. Administering sugar to a subject provides a carbon source for producing acetyl groups and administering the Krebs cycle intermediate or the precursor of a Krebs cycle intermediate to a subject increases the concentration of the particular Krebs cycle intermediate at the mitochondrial level. It is believed that this has a priming effect, because a four carbon intermediate is needed in order for the two-carbon derivatives of glucose and other substrates to enter the Krebs cycle. Specifically, the two-carbon acetyl group must combine with the four-carbon oxaloacetate to form citrate in order for the Krebs cycle to continue. Malate is in equilibrium with oxaloacetate, and other Krebs cycle intermediates are readily converted to malate and oxaloacetate. The conversion of succinate and fumarate to malate and oxaloacetate is particularly rapid. Metabolically compromised cells tend to utilize Krebs cycle intermediates for the direct generation of energy. More specifically, they utilize the intermediates to generate electrons which then generate ATP through electron transport. While utilizing the intermediates provides an immediate source of energy, doing so compromises the subsequent activity of the Krebs cycle. Administration of the pharmaceutical compositions of the present invention is believed, therefore to prime the Krebs cycle so that it again operates efficiently.

Thus, another aspect of the present invention relates to a method of treating a subject having a disorder involving impaired mitochondrial function. Generally, the method includes administering the pharmaceutical composition of the present invention to a subject under conditions effective to improve mitochondrial function.

This method of the present invention is particularly useful for the treatment or prophylaxis of disorders associated with impaired mitochondrial function. Disorders that can be treated according to this method generally include conditions or diseases characterized by a decreased level of oxidative metabolism. The disorders may be caused by genetic factors, environmental factors, or both. More specifically, such disorders include conditions or diseases of the nervous system (e.g., neurodegenerative, psychoses, etc.), conditions or diseases of other parts of the body, and conditions or diseases of the body as a whole. Exemplary conditions or diseases of the nervous system include Alzheimer's Disease, Parkinson's Disease, Huntington's Disease, spinocerebellar ataxias, and psychoses (including depression or schizophrenia) associated with oxidative metabolic abnormalities. Exemplary conditions or disorders of other parts of the body include cardiovascular disorders (e.g., atherosclerotic and cardiovascular diseases including myocardial infarctions, angina, cardiomyopathies, cardiac valvular disorders, and other conditions or disorders causing cardiac failure), musculoskeletal disorders in which oxidative metabolism is abnormal (De Coo et al., A Mitochondrial tRNA(Val) Gene Mutation (G1642A) in a Patient With Mitochondrial Myopathy, Lactic Acidosis, and Stroke-like Episodes," *Neurol.* 50:293–295 (1998), which is hereby incorporated by reference), and other conditions or disorders of non-neural tissues in which oxidative metabolism is abnormal, such as frailty, which is a recognized geriatric syndrome often associated with metabolic alterations (Fayette et al., *Eur. J. Clin. Nutrition* 52:45–53 (1998), which is hereby incorporated by reference).

Many conditions or diseases of the nervous system (e.g., AD and those described above) are characterized by cerebral metabolic insufficiencies, which are manifested as impaired cerebral function such as dementia. Therefore, another aspect of the present invention relates to a method of improving cerebral function in a subject having cerebral metabolic insufficiencies. Generally, a pharmaceutical composition of the present invention is administered to a subject having impaired cerebral metabolism under conditions effective to improve the cerebral cellular metabolism. By improving cerebral cellular metabolism, the subject's cerebral function is improved significantly.

Treatment for nervous system disorders typically involves administration of the pharmaceutical composition of the present invention so that the Krebs cycle intermediate or the precursor of a Krebs cycle intermediate is introduced into brain tissue. To exert its desired therapeutic or prophylactic effects, the sugar and the Krebs cycle intermediate or the precursor of a Krebs cycle intermediate must be transported into the brain cells and subsequently the Krebs cycle intermediate and derivatives of the sugar (e.g., pyruvate, acetate) must be incorporated into the brain cell mitochondria (i.e., where they may be incorporated into the Krebs cycle).

Depending upon how the pharmaceutical composition of the present invention is administered (e.g., oral dosage, intravenous injection, etc.) and the conditions of the patient to be treated, effective administration may require overcoming the cerebrovascular endothelium, also called the blood-brain barrier ("BBB"). The BBB is formed by cerebral endothelial cells under the influence of astroglial cells of the brain (Johansson, "Experimental Models of Altering the Blood Brain Barrier," *Progress in Brain Research*, 91:171–175 (1992); Ermisch, "Peptide Receptors of the Blood-Brain Barrier and Substrate Transport into the Brain," *Progress in Brain Research*, 91:155–161 (1992), which are hereby incorporated by reference). Briefly, the BBB contains a monolayer of tightly connected microvascular endothelial cells with anionic charges. This layer separates two fluid-containing compartments: the blood plasma and extracellular fluid of the brain parenchyma. One of the main functions of the BBB is to regulate the transfer of components between blood plasma and extracellular fluid. The BBB limits free passage of molecules from the blood to the brain cells. This limited penetration into the CNS is noticeable with large molecules of high polarity such as protein conjugates, enzymes, etc. (Bobo et al., "Convection-enhanced Delivery of Macromolecules in the Brain," *Proc. Natl. Acad. Sci. USA*, 91:2076–2080 (1994), which is hereby incorporated by reference).

According to a first approach, the Krebs cycle intermediate or the precursor of a Krebs cycle intermediate is administered in a form which more readily crosses the BBB and enters individual brain cells. For example, mono- or di-alkyl esters of Krebs cycle intermediates (e.g., malate esters) are particularly preferred. Without being bound to a particular theory, it is believed that the ester precursors are more lipophilic and, therefore, more likely to cross the BBB. See U.S. Pat. No. 5,739,117 to Yokoyama, which is hereby incorporated by reference.

According to another approach, the BBB is circumvented according to any of a variety of known strategies, for example, intrathecal injections (Ommaya, "Implantable Devices for Chronic Access and Drug Delivery to the Central Nervous System," *Cancer Drug Delivery*, 1(2): 169–179 (1984), which is hereby incorporated by reference), surgical implants (U.S. Pat. No. 5,222,982 to Ommaya ,which is hereby incorporated by reference), and interstitial infusion (Bobo et al., "Convection-enhanced Delivery of Macromolecules in the Brain," *Proc. Natl. Acad. Sci. USA*, 91:2076–2080 (1994), which is hereby incorporated by reference). Each of these strategies involve delivery of the Krebs cycle intermediate or the precursor of a Krebs cycle intermediate to the central nervous system by direct administration into the cerebrospinal fluid or into the brain parenchyma.

According to a third approach, the Krebs cycle intermediate or the precursor of a Krebs cycle intermediate is linked to a molecule which enhances crossing of the BBB. Various BBB crossing enhancers have been identified (e.g., permeabilizer peptides), and others are constantly being identified.

As described above, the pharmaceutical composition of the present invention is useful for treating a subject having a nervous system disorder which involves impaired mitochondrial function. Several nervous system disorders are known to involve deficiencies in neurotransmitter systems. For example, AD is associated with degeneration of cholinergic neurons in the basal forebrain that play a fundamental role in cognitive functions, including memory (Becker et al., "Mechanisms of Cholinesterase Inhibition in Senile Dementia of the Alzheimer Type: Clinical, Pharmacological, and Therapeutic Aspects," *Drug Dev. Res.* 12: 163–195 (1988)). As a result of such degeneration, patients suffering from the disease exhibit a marked reduction in acetylcholine synthesis, choline acetyltransferase activity, acetylcholinesterase activity and choline uptake. There have been several approaches employed to treat AD. These generally include the administration of acetylcholinesterase inhibitors or acetylcholine synthesis, storage or release modulators. Also, since activation of NMDA glutamate receptors has also been implicated in the etiologies of HD, amyotrophic lateral sclerosis, olivopontocerebellar atrophy and AD, use of NMDA glutamate receptor antagonists may be of clinical benefit for patients having these disorders (Woodruff et al., "The Interaction Between MK-801 and Receptors for N-methyl-D-aspartate: Functional Consequences," *Neuropharm.* 26:903–909 (1987); Greenamyre et al., "N-methyl-D-aspartate Antagonists in the Treatment of Parkinson's Disease," *Arch. Neurol.* 48:977–981 (1991); Giuffra et al., "Glutamatergic Therapy of Huntington's Chorea," *Clin. Neuropharm.* 15:148–151 (1992), which are hereby incorporated by reference), as well as for patients suffering from certain neurodegenerative effects of aging (Ferris, S. H. "Therapeutic Strategies in Dementia Disorders" *Acta Neurol. Scand.* 129(Suppl.):23–26 (1990), which is hereby incorporated by reference). With respect to agents used in the treatment of PD, L-dopa and its derivatives are primary therapeutic agents.

For treatment of certain nervous system disorders, therefore, the pharmaceutical composition of the present invention can be administered alone or in combination with a therapeutic agent for the treatment of a nervous system disorder. Suitable therapeutic agents include conventional medications for treating such nervous system disorders. By way of example, for treatment of AD, the pharmaceutical composition can be administered in combination with either an acetylcholinesterase inhibitor, an acetylcholine synthesis, storage or release modulator, an NDMA glutamate receptor antagonist, or combinations thereof. A number of suitable acetylcholinesterase inhibitors, acetylcholine synthesis, storage or release modulators, and NDMA glutamate receptor antagonists are currently known and others are continually being discovered and reported.

As described above, the pharmaceutical composition of the present invention is useful for treating a subject having a cardiovascular disorder which involves impaired mitochondrial function. For treatment of certain cardiovascular disorders, therefore, the pharmaceutical composition of the present invention can be administered alone or in combination with conventional agents for the treatment of cardiovascular disorders. By way of example, the pharmaceutical composition of the present invention can be administered simultaneously with either blood-thinners, cholesterol lowering agents, anti-platelet agents, vasodilators, beta-blockers, angiotensin blockers, digitalis and its derivatives, and combinations thereof. A number of suitable blood-thinners, cholesterol lowering agents, anti-platelet agents, vasodilators, beta-blockers, angiotensin blockers, and digitalis derivatives are currently known and others are continually being discovered and reported.

As described above, the pharmaceutical composition of the present invention is useful for treating a subject having a musculoskeletal disorder which involves impaired mitochondrial function. For treatment of certain musculoskeletal disorders, therefore, the pharmaceutical composition of the present invention can be administered alone or in combination with conventional agents for the treatment of musculoskeletal disorders.

EXAMPLES

The following Examples are provided to illustrate embodiments of the present invention but are by no means intended to limit its scope.

Example 1
Treating Alzheimer's Disease with Administration of Supplemental Malic Acid and Glucose Malic acid was administered to seven (7) patients with Alzheimer's Disease in an open study. The longest any patient received malic acid was sixteen weeks. Each of the patients received 15 grams of malic acid per day, which was administered by dissolving the malic acid in unsweetened grape juice, which naturally contains glucose. The addition of the malic acid to the unsweetened grape juice resulted in a sour tasting liquid.

Compliance in ingesting this sour liquid was variable. One patient, excluded from the results described herein, simply refused to ingest the formulation of the malic acid in unsweetened grape juice. The malic acid and glucose were administered simultaneously with "best available therapy," which included Aricept® (available from Eisai Inc., Teaneck, N.J., and Pfizer Inc., New York, N.Y.) in 6 of the 7 patients (Patients 1 and 3–7).

Cognition was measured by the widely-used and robust Mini-Mental State Examination ("MMSE") (Folstein et al., "Mini-Mental State: A Practical Method for Grading Cognitive States of Patients for the Clinician," *J. Psychiat. Res.* 12:189–198 (1975), which is hereby incorporated by reference. The MMSE is divided into two sections. The first section requires only vocal responses and tests the patient's orientation, memory, and attention. The second section tests the patient's ability to name, follow verbal and written commands, write a sentence spontaneously, and copy a complex polygon. The maximum score on the first section is 21 and the maximum score on the second section is 9, for a maximum total score of 30. Higher scores on the MMSE indicate better performance. Scores of 28–30 indicate normal intelligence, scores of 23 or below indicate dementia, and scores of 9 or below indicate severe dementia.

Patients were tested using the MMSE prior to beginning treatment with the malic acid and glucose supplement and again after cessation of the supplement. Results are shown in Table 1 below.

TABLE 1

Treatment of Alzheimer's Disease Patients with Malic Acid and Glucose

| Patient | Treatment Duration (weeks) | MMSE Score Before Treatment | MMSE Score After Treatment | Change |
|---|---|---|---|---|
| 1 | 10 | 9 | 16 | 7 |
| 2 | 12 | 6 | 13 | 7 |
| 3 | 16 | 25 | 29 | 4 |
| 4 | 2 | 24 | 28 | 4 |
| 5 | 12 | 9 | 13 | 4 |
| 6 | 16 | 9 | 18 | 9 |
| 7 | 2 | 20 | 24 | 4 |

The net result was an improvement (increase) in MMSE score. The improvement was statistically significant, as analyzed using the paired t-test (P=0.00039, two-tailed). In three patients, the MMSE scores changed dramatically, and for the remaining four patients, MMSE scores showed modest advances. All of the patients assessed on a care-giver rating scale of function. While behavioral ratings were more variable than cognitive scores, each of the above patients were described by their (s) as also improving behaviorally.

Example 2
Treating Alzheimer's Disease with Administration of Supplemental Malic Acid Alone In three patients from Example 1, the nutritional supplement was replaced with capsules containing the same amount of malic acid previously taken in the form dissolved in grape juice. All three patients deteriorated markedly within two weeks. In one of these patients, the MMSE score fell from 17 to 12. Relatives of these patients requested that the patients go back on the original formulation.

These observations indicate the beneficial results were not due primarily to a placebo effect, since both the patients and the health care professional conducting the study expected that the patients would do better on the capsules than on the original formulation. These observations also indicate that the beneficial effect is due to the pharmaceutical composition of the present invention, rather than a Krebs cycle intermediate alone.

Example 3

Treatment of Psychoses with Administration of Supplemental Malic Acid and Glucose Two patients who had been clinically diagnosed with depression were under supervised care with conventional treatment. Each of the patients received 15 grams of malic acid per day, which was administered by dissolving the malic acid in unsweetened grape juice, which naturally contains glucose.

Patient No. 1

A 58 year old woman with a long history of dysthymia with intermittent depression and withdrawal, and a strong family history with schizophrenia, was on maintenance treatment with a selective serotonin reuptake inhibitor, namely Zoloft (50 mg/day). After two weeks on the malic acid and glucose nutritional supplement, she was happier and more active, claiming she no longer needed any other medication. These added beneficial effects were maintained during the month that she was taking the nutritional supplement, and disappeared within a few days after it was discontinued.

Patient No. 2

A 60 year old man with a strong family history of depression was on maintenance therapy for recurrent depression with an SSRI (Prozac 40 mg/day). After two weeks on the pharmaceutical composition containing malic acid and glucose, the man felt more calm and less pressured. While taking the pharmaceutical composition, the Prozac was reduced to 20 mg/day without deterioration of function. After stopping administration of the pharmaceutical composition, he again required 40 mg/day Prozac.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A pharmaceutical composition comprising glucose, malic acid, and resveratrol.

2. The pharmaceutical composition according to claim 1 further comprising:
   a pharmaceutically acceptable vehicle.

3. The pharmaceutical composition according to claim 1 further comprising:
   an adjuvant for enhancing mitochondrial function.

4. The pharmaceutical compositions according to claim 3, wherein the adjuvant is selected from a group consisting of a vitamin, a mineral, an antioxidant other than resveratrol, a metabolism-enhancing compound, and mixtures thereof.

5. The pharmaceutical composition according to claim 4, wherein the metabolism-enhancing compound is selected from a group consisting of creatine, L-carnitine, L-carnitine derivatives, and mixtures thereof.

6. The pharmaceutical composition according to claim 4, wherein the vitamin is selected from a group consisting of thiamin, riboflavin, niacin, pyridoxine derivatives, pantothenic acid, and mixtures thereof.

7. The pharmaceutical composition according to claim 4, wherein the mineral is selected from a group consisting of calcium, magnesium, sodium, potassium, zinc, and mixtures thereof.

8. The pharmaceutical composition according to claim 4, wherein the antioxidant is selected from a group consisting of ascorbic acid, alpha tocopherol, quercetin, and mixtures thereof.

9. The pharmaceutical composition according to claim 1 further comprising a sugar other than glucose.

10. The pharmaceutical composition according to claim 1 further comprising a Krebs cycle intermediate other than malic acid.

11. A method of treating impaired mitochondrial function comprising:
    administering a pharmaceutical composition according to claim 1, to a subject having a disorder involving impaired mitochondrial function under conditions effective to improve mitochondrial function.

12. The method according to claim 11 further comprising:
    administering an adjuvant for enhancing mitochondrial function.

13. The method according to claim 12, wherein the adjuvant is selected from a group consisting of a vitamin, a mineral, an antioxidant other than resveritrol, a metabolism-enhancing compound, and mixtures thereof.

14. The method according to claim 11, wherein said administering is oral, parenteral, subcutaneous, intravenous, intramuscular, intraperitoneal, by intranasal instillation, or by application to mucous membranes.

15. The method according to claim 11, wherein the pharmaceutical composition is administered to a patient suffering from a nervous system disorder, a cardiovascular disorder, a musculoskeletal disorder, or a disorder of the body as a whole.

16. The method according to claim 15, wherein the nervous system disorder is Alzheimer's Disease, Huntington's Disease, Parkinson's Disease, spinocerebellar ataxia, or a psychosis.

17. The method according to claim 16, wherein the nervous system disorder is Alzheimer's Disease.

18. The method according to claim 17 further comprising:
    administering a therapeutic agent selected from a group consisting of an acetylcholinesterase inhibitor, acetylcholine synthesis modulator, acetylcholine storage modulator, acetylcholine release modulator, and NMDA glutamate receptor antagonist.

19. The method according to claim 16, wherein the nervous system disorder is Huntington's Disease.

20. The method according to claim 19 further comprising:
    administering an NMDA glutamate receptor antagonist in conjunction with the pharmaceutical composition.

21. The method according to claim 15, wherein the cardiovascular disorder is selected from a group consisting of atherosclerotic cardiovascular disease, cardiomyopathies, cardiac valvular disorders, and disorders causing cardiac failure.

22. The method according to claim 15, wherein the disorder of the body as a whole is frailty.

23. A method of improving cerebral function in a subject having impaired cerebral metabolism comprising:
    administering a pharmaceutical composition according to claim 1 to a subject having impaired cerebral metabolism under conditions effective to improve cerebral function.

24. The method according to claim 23 further comprising:
administering an adjuvant for enhancing cerebral function.

25. The method according to claim 24, wherein the adjuvant is selected from a group consisting of a vitamin, a mineral, an antioxidant, a metabolism-enhancing compound, and mixtures thereof.

26. The method according to claim 23, wherein said administering is oral, parenteral, subcutaneous, intravenous, intramuscular, intraperitoneal, by intranasal instillation, or by application to mucous membranes.

27. A pharmaceutical composition consisting essentially of glucose and malic acid.

28. The pharmaceutical composition according to claim 27 further consisting essentially of a sugar other than glucose.

29. The pharmaceutical composition according to claim 27 further consisting essentially of a Krebs cycle intermediate other than malic acid.

30. A method of treating impaired mitochondrial function comprising:
administering a pharmaceutical composition according to claim 27 to a subject having a disorder involving impaired mitochondrial function under conditions effective to improve mitochondrial function.

31. The method according to claim 30 further comprising:
administering an adjuvant for enhancing mitochondrial function.

32. The method according to claim 31, wherein the adjuvant is selected from a group consisting of a vitamin, a mineral, an antioxidant, a metabolism-enhancing compound, and mixtures thereof.

33. The method according to claim 30, wherein the pharmaceutical composition is administered to a patient suffering from a nervous system disorder, a cardiovascular disorder, a musculoskeletal disorder, or a disorder of the body as a whole.

34. The method according to claim 33, wherein the nervous system disorder is Alzheimer's Disease, Huntington's Disease, Parkinson's Disease, spinocerebellar ataxia, or a psychosis.

35. The method according to claim 34, wherein the nervous system disorder is Alzheimer's Disease.

36. The method according to claim 35 further comprising:
administering a therapeutic agent selected from a group consisting of an acetylcholinesterase inhibitor, acetylcholine synthesis modulator, acetylcholine storage modulator, acetylcholine release modulator, and NMDA glutamate receptor antagonist.

37. The method according to claim 34, wherein the nervous system disorder is Huntington's Disease.

38. The method according to claim 37 further comprising:
administering an NMDA glutamate receptor antagonist in conjunction with the pharmaceutical composition.

39. The method according to claim 33, wherein the cardiovascular disorder is selected from a group consisting of atherosclerotic cardiovascular disease, cardiomyopathies, cardiac valvular disorders, and disorders causing cardiac failure.

40. The method according to claim 33, wherein the disorder of the body as a whole is frailty.

41. The method according to claim 30, wherein said administering is oral, parenteral, subcutaneous, intravenous, intramuscular, intraperitoneal, by intranasal instillation, or-by application to mucous membranes.

42. A method of improving cerebral function in a subject having impaired cerebral metabolism comprising:
administering a pharmaceutical composition according to claim 27, to a subject having impaired cerebral metabolism under conditions effective to improve cerebral function.

43. The method according to claim 42 further comprising:
administering an adjuvant for enhancing cerebral function.

44. The method according to claim 43, wherein the adjuvant is selected from a group consisting of a vitamin, a mineral, an antioxidant, a metabolism-enhancing compound, and mixtures thereof.

45. The method according to claim 42, wherein said administering is oral, parenteral, subcutaneous, intravenous, intramuscular, intraperitoneal, by intranasal instillation, or by application to mucous membranes.

* * * * *